US012667665B2

(12) United States Patent
Zheng et al.

(10) Patent No.: US 12,667,665 B2
(45) Date of Patent: Jun. 30, 2026

(54) TECHNIQUES AND DEVICES THAT ADAPT BASAL PROFILES FOR DRUG DELIVERY APPLICATIONS

(71) Applicant: Insulet Corporation, Acton, MA (US)

(72) Inventors: Yibin Zheng, Harland, WI (US); Joon Bok Lee, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 1118 days.

(21) Appl. No.: 17/578,716

(22) Filed: Jan. 19, 2022

(65) Prior Publication Data

US 2022/0241503 A1 Aug. 4, 2022

Related U.S. Application Data

(60) Provisional application No. 63/143,171, filed on Jan. 29, 2021.

(51) Int. Cl.
    *A61M 5/172* (2006.01)
    *A61M 5/142* (2006.01)
(52) U.S. Cl.
    CPC ...... *A61M 5/1723* (2013.01); *A61M 5/14244* (2013.01); *A61M 2205/52* (2013.01)
(58) Field of Classification Search
    CPC ............ A61M 5/1723; A61M 5/14244; A61M 2205/52; A61M 5/172; A61M 5/14248
    See application file for complete search history.

(56) References Cited

U.S. PATENT DOCUMENTS

| | | | |
|---|---|---|---|
| 303,013 | A | 8/1884 | Horton |
| 2,797,149 | A | 6/1957 | Skeggs |
| 3,631,847 | A | 1/1972 | Hobbs |
| 3,634,039 | A | 1/1972 | Brondy |
| 3,812,843 | A | 5/1974 | Wootten et al. |
| 3,841,328 | A | 10/1974 | Jensen |
| 3,963,380 | A | 6/1976 | Thomas, Jr. et al. |
| 4,055,175 | A | 10/1977 | Clemens et al. |
| 4,146,029 | A | 3/1979 | Ellinwood, Jr. |
| 4,151,845 | A | 5/1979 | Clemens |

(Continued)

FOREIGN PATENT DOCUMENTS

| | | |
|---|---|---|
| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)

(Continued)

*Primary Examiner* — Bhisma Mehta
*Assistant Examiner* — Marissa Taylor
(74) *Attorney, Agent, or Firm* — Goodwin Procter LLP

(57) ABSTRACT

The disclosed examples provide techniques and devices for determining a daily basal profile or an adjusted basal need for a drug based on a collection of data that is filtered and processed. A controller may be configured to evaluate a history of drug delivery in both basal and bolus dosages and generate a daily basal profile or an adjusted basal need that is a time dependent that may be used to schedule basal dosages of a drug that more closely addresses a user's drug needs over the course of a time period, such as a day, week or the like.

20 Claims, 4 Drawing Sheets

(56)     References Cited

U.S. PATENT DOCUMENTS

| | | | |
|---|---|---|---|
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |

(56)                 References Cited

U.S. PATENT DOCUMENTS

| | | | |
|---|---|---|---|
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |

(56)                 References Cited

U.S. PATENT DOCUMENTS

| | | |
|---|---|---|
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1* | 5/2007 | Campbell ......... A61M 5/14248 705/2 |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |

(56)  References Cited

U.S. PATENT DOCUMENTS

| | | |
|---|---|---|
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1* | 3/2019 | Grosman ............ A61B 5/4839 |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0016006 A1* | 1/2021 | El-Khatib ............ G16H 20/60 |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 2139382 A1 | 1/2010 |
| EP | 2397181 A1 | 12/2011 |
| EP | 2666520 A1 | 11/2013 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 1571582 B1 | 4/2019 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 200032258 A1 | 6/2000 |
| WO | 0172354 A2 | 10/2001 |
| WO | 2002015954 A1 | 2/2002 |
| WO | 2002043866 A2 | 6/2002 |

(56) References Cited

FOREIGN PATENT DOCUMENTS

| WO | 2002082990 A1 | 10/2002 |
|----|---------------|---------|
| WO | 2003016882 A1 | 2/2003 |
| WO | 2003039362 A1 | 5/2003 |
| WO | 2003045233 A1 | 6/2003 |
| WO | 2004043250 A1 | 5/2004 |
| WO | 2005110601 A1 | 5/2004 |
| WO | 2004092715 A1 | 10/2004 |
| WO | 2005051170 A2 | 6/2005 |
| WO | 2005082436 A1 | 9/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple, and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination Of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 Vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al., "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010 (OPTIS.247VPC).

International Search Report and Written Opinion in PCT/US2008/079641 (Optis.203VPC) dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et al., "Clinical Performance of an In line Ex-Vivo Point of Care Monitor: A Multicenter Study," Clinical Chemistry 48: 11, pp. 2030-2043, 2002.

(56) References Cited

OTHER PUBLICATIONS

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, mailed May 16, 2017, 12 pages.

International Search Report and Written Opinion for the International Patent Application No. PCT/US2018/018901, mailed on Aug. 6, 2018, 12 pages.

International Search Report and Written Opinion for International Patent Application No. PCT/US2018/052467, mailed Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.

"Read NFC Tags with an iPHone App on IOS 11", GoToTags, Sep. 11, 2017, web <https://gototags.com/blog/read-nfc-tags-with-an-iphone-app-on-ios-11/> (Year:2017).

International Search Report and Written Opinion for International Patent Application No. PCT/US2016/063350, mailed on Mar. 27, 2017, 9 pages.

Extended Search Report mailed Aug. 13, 2018, issued in European Patent Application No. 16753053.4, 9 pages.

International Search Report and Written Opinion for International Patent Application No. PCT/US16/18452, mailed on Apr. 29, 2015, 9 pages.

International Preliminary Report on Patentability mailed Aug. 31, 2017, issued in PCT Patent Application No. PCT/US2016/018452, 7 pages.

(56)                    References Cited

OTHER PUBLICATIONS

International Search Report and Written Opinion for International Patent Application No. PCT/US2019/055862, mailed on Mar. 11, 2020.

International Search Report and Written Opinion for Application No. PCT/US2019/030562, Sep. 25, 2019, 19 pages.

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Patent Office, "Notification of Transmittal of the ISR and the Written Opinion of the International Searching Authority, or the Declaration," in PCT Application No. PCT/GB2015/050248, Jun. 23, 2015, 12 pages.

International Search Report and Written Opinion for the International Patent Application No. PCT/US2021/012246, mailed Apr. 13, 2021, 15 pages.

International Search Report and Written Opinion for the International Patent Application No. PCT/US2021/013639, mailed Apr. 28, 2021, 14 pages.

International Search Report and Written Opinion for the International Patent Application No. PCT/US2020/063326, mailed May 3, 2021, 17 pages.

European Search Report for the European Patent Application No. 21168591, mailed Oct. 13, 2021, 4 pages.

International Search Report and Written Opinion for the International Patent Application No. PCT/US2021/041954, mailed Oct. 25, 2021, 13 pages.

International Search Report and Written Opinion for the International Patent Application No. PCT/US2021/022694, mailed Jun. 25, 2021, 13 pages.

International Search Report and Written Opinion for the International Patent Application No. PCT/US2021/017664, mailed May 26, 2021, 16 pages.

International Search Report and Written Opinion for the International Patent Application No. PCT/US2022/012896, mailed Apr. 22, 2022, 15 pages.

International Search Report and Written Opinion for the International Patent Application No. PCT/US2022/013470, mailed May 6, 2022, 14 pages.

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

International Search Report and Written Opinion for the International Patent Application No. PCT/US22/018700, mailed Jun. 7, 2022, 13 pages.

International Search Report and Written Opinion for the International Patent Application No. PCT/US22/019080, mailed Jun. 7, 2022, 14 pages.

International Search Report and Written Opinion for the International Patent Application No. PCT/US22/019664, mailed Jun. 7, 2022, 14 pages.

International Search Report and Written Opinion for International Patent Application No. PCT/US2021/051027, mailed on Jan. 7, 2022, 16 pages.

International Search Report and Written Opinion for International Patent Application No. PCT/US2021/052372, mailed Jan. 26, 2022, 15 pages.

International Search Report and Written Opinion for the International Patent Application No. PCT/US2021/046607, mailed Jan. 31, 2022, 20 pages.

International Search Report and Written Opinion for the International Patent Application No. PCT/US2021/055745, mailed Feb. 14, 2022, 13 pages.

International Search Report and Written Opinion for the International Patent Application No. PCT/US21/060618, mailed Mar. 21, 2022, 15 pages.

Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (2019-11-09), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/ blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

International Search Report and Written Opinion for the International Patent Application No. PCT/US2021/052855, mailed Dec. 22, 2021, 11 pages.

International Search Report and Written Opinion for the International Patent Application No. PCT/US2021/047771, mailed Dec. 22, 2021, 11 pages.

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

* cited by examiner

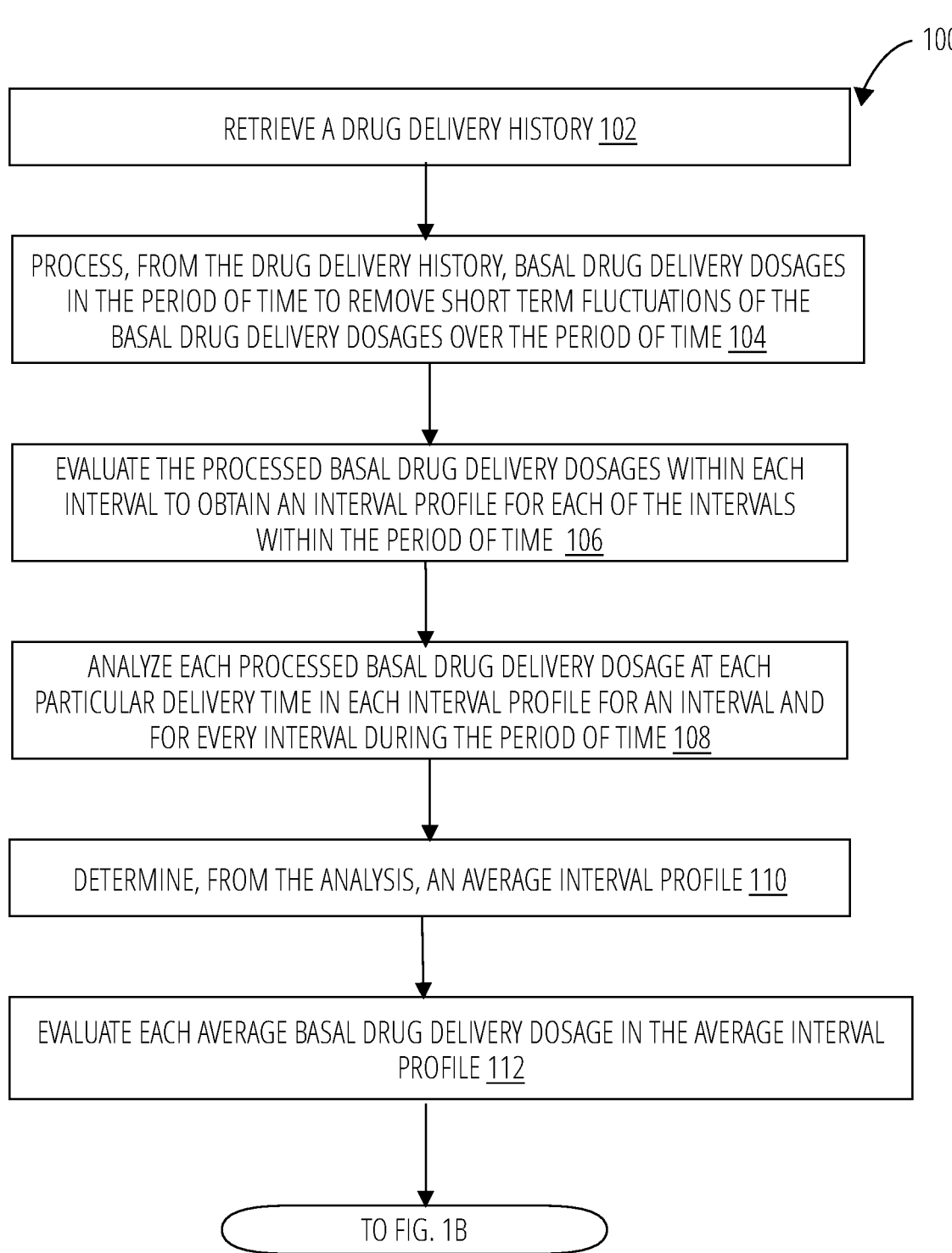

100

RETRIEVE A DRUG DELIVERY HISTORY 102

PROCESS, FROM THE DRUG DELIVERY HISTORY, BASAL DRUG DELIVERY DOSAGES IN THE PERIOD OF TIME TO REMOVE SHORT TERM FLUCTUATIONS OF THE BASAL DRUG DELIVERY DOSAGES OVER THE PERIOD OF TIME 104

EVALUATE THE PROCESSED BASAL DRUG DELIVERY DOSAGES WITHIN EACH INTERVAL TO OBTAIN AN INTERVAL PROFILE FOR EACH OF THE INTERVALS WITHIN THE PERIOD OF TIME 106

ANALYZE EACH PROCESSED BASAL DRUG DELIVERY DOSAGE AT EACH PARTICULAR DELIVERY TIME IN EACH INTERVAL PROFILE FOR AN INTERVAL AND FOR EVERY INTERVAL DURING THE PERIOD OF TIME 108

DETERMINE, FROM THE ANALYSIS, AN AVERAGE INTERVAL PROFILE 110

EVALUATE EACH AVERAGE BASAL DRUG DELIVERY DOSAGE IN THE AVERAGE INTERVAL PROFILE 112

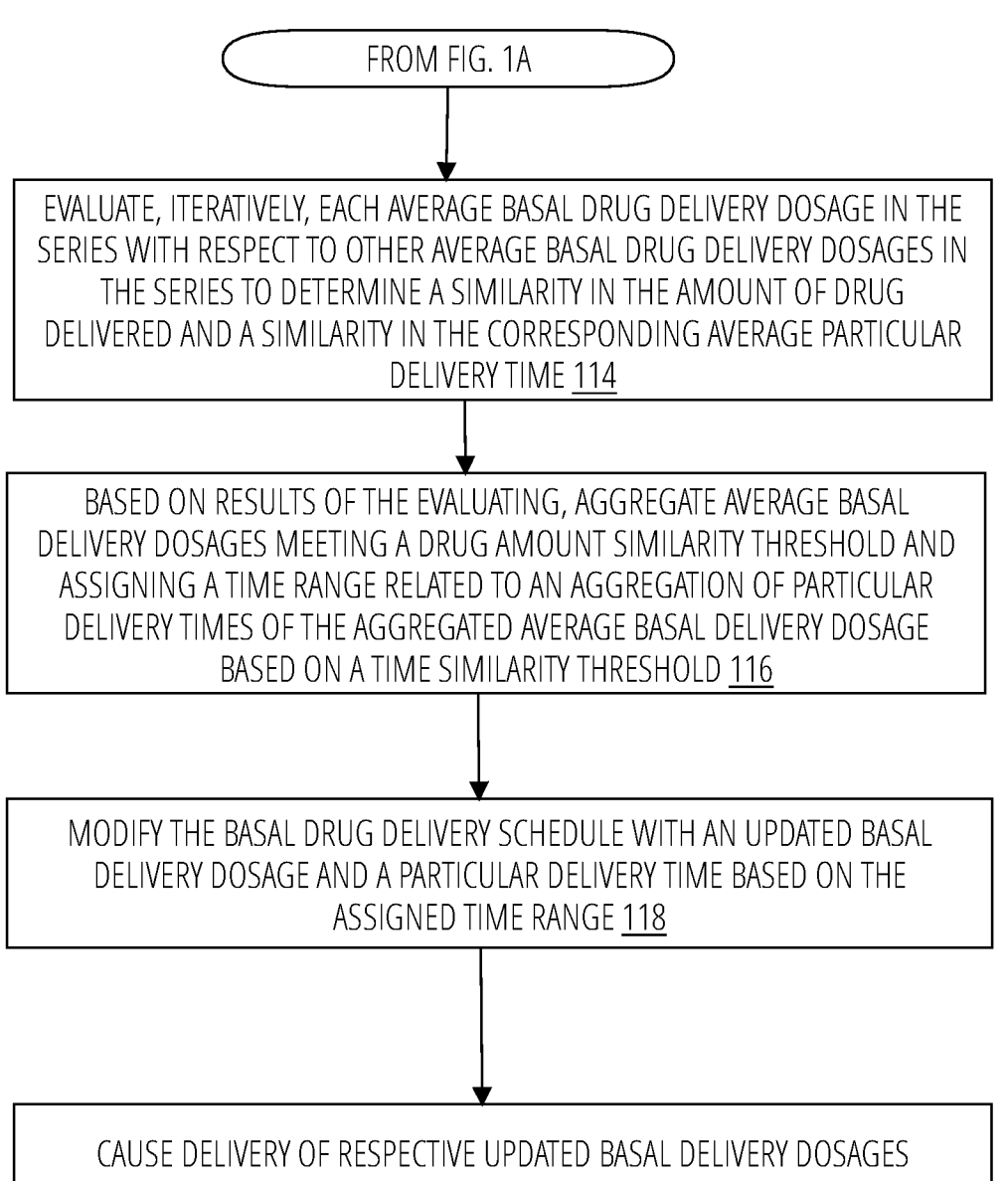

FROM FIG. 1A

EVALUATE, ITERATIVELY, EACH AVERAGE BASAL DRUG DELIVERY DOSAGE IN THE SERIES WITH RESPECT TO OTHER AVERAGE BASAL DRUG DELIVERY DOSAGES IN THE SERIES TO DETERMINE A SIMILARITY IN THE AMOUNT OF DRUG DELIVERED AND A SIMILARITY IN THE CORRESPONDING AVERAGE PARTICULAR DELIVERY TIME 114

BASED ON RESULTS OF THE EVALUATING, AGGREGATE AVERAGE BASAL DELIVERY DOSAGES MEETING A DRUG AMOUNT SIMILARITY THRESHOLD AND ASSIGNING A TIME RANGE RELATED TO AN AGGREGATION OF PARTICULAR DELIVERY TIMES OF THE AGGREGATED AVERAGE BASAL DELIVERY DOSAGE BASED ON A TIME SIMILARITY THRESHOLD 116

MODIFY THE BASAL DRUG DELIVERY SCHEDULE WITH AN UPDATED BASAL DELIVERY DOSAGE AND A PARTICULAR DELIVERY TIME BASED ON THE ASSIGNED TIME RANGE 118

CAUSE DELIVERY OF RESPECTIVE UPDATED BASAL DELIVERY DOSAGES ACCORDING TO THE MODIFIED BASAL DRUG DELIVERY SCHEDULE VIA A PUMP MECHANISM COMMUNICATIVELY COUPLED TO THE CONTROLLER 120

FIG. 1B

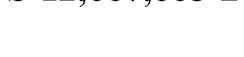
200

ACCESS, BY A CONTROLLER OF A DRUG DELIVERY DEVICE, A DRUG DELIVERY HISTORY, A BOLUS DRUG HISTORY, A BLOOD GLUCOSE MEASUREMENT HISTORY, AND A MEAL ANNOUNCEMENT HISTORY FOR A PERIOD OF TIME 202

FILTER, BY THE RESPECTIVE CONTROLLER, RESPECTIVE DATA IN EACH OF THE DRUG DELIVERY HISTORY, THE BOLUS DRUG HISTORY, THE BLOOD GLUCOSE MEASUREMENT HISTORY, AND THE MEAL ANNOUNCEMENT HISTORY, ACCORDING TO PREDETERMINED FILTER SETTINGS RELATED TO A TIME SEGMENT OF THE PERIOD OF TIME 204

CALCULATE A DAILY BASAL PROFILE USING THE FILTERED RESPECTIVE DATA FROM EACH OF THE DRUG DELIVERY HISTORY, THE BOLUS DRUG HISTORY, THE BLOOD GLUCOSE MEASUREMENT HISTORY, AND THE MEAL ANNOUNCEMENT HISTORY 206

GENERATE, BY THE CONTROLLER, A CONTROL SIGNAL FOR DELIVERY OF A BASAL DOSAGE OF THE CALCULATED BASAL DELIVERY DOSAGES AT A SCHEDULED TIME FROM THE DAILY BASAL PROFILE 208

OUTPUT THE CONTROL SIGNAL TO A PUMP MECHANISM OF THE DRUG DELIVERY DEVICE COMMUNICATIVELY COUPLED TO THE CONTROLLER 210

FIG. 2

TECHNIQUES AND DEVICES THAT ADAPT BASAL PROFILES FOR DRUG DELIVERY APPLICATIONS

RELATED APPLICATIONS

This application claims the benefit of U.S. Provisional Patent Application No. 63/143,171, filed Jan. 29, 2021, the contents of which are incorporated herein by reference in their entirety.

BACKGROUND

A number of systems provide basal delivery of drugs, such as insulin, chemotherapy drugs, pain management drugs and the like. Throughout a day, the basal insulin needed for any diabetic user to maintain a stable fasting glucose target setting varies 20-30% or more at different times. A time dependent basal profile is therefore a key system setting that the system should learn and adapt to.

A key challenge of this problem is that carbohydrate intake and bolus delivery of drugs, such as insulin and glucagon are confounding factors in basal insulin to glucose relationship. There is a need for methods and devices that compensate for the impact of such confounding factors to arrive at more accurate estimates of a basal drug delivery profile.

SUMMARY

In one aspect, a method is disclosed that includes retrieving, by a controller on a wearable drug delivery device, a drug delivery history that is a collection of basal drug delivery dosages delivered according to a basal drug delivery schedule. The drug delivery history may include a predetermined number of basal drug delivery dosages of a drug delivered over a period of time. The period of time may be further partitioned into intervals that span a time range less than the period of time. The drug delivery schedule may include a particular delivery time for each basal drug delivery dosage in the collection during each respective interval, and each basal drug delivery dosage in the collection is an amount of the drug delivered at the particular delivery time during each respective interval and each particular delivery time is one point in time during the interval. The controller processes the basal drug delivery dosages in the period of time to remove short term fluctuations of the basal drug delivery dosages over the period of time. The processed basal drug delivery dosages within each interval may be evaluated to obtain an interval profile for each of the intervals within the period of time. The interval profile is a data structure including the amount of the drug delivered in each processed basal drug delivery dosage and the particular delivery time associated with each processed basal drug delivery dosage during the interval. In the example method, each processed basal drug delivery dosage may be analyzed at each particular delivery time in each interval profile for an interval and for every interval during the period of time. From the analysis, an average interval profile may be determined. The average interval profile may contain a series of average basal drug delivery dosages where each average basal drug delivery dosage in the series has a corresponding average particular delivery time. The controller may iteratively evaluate each average basal drug delivery dosage in the series with respect to other average basal drug delivery dosages in the series to determine a similarity in the amount of drug delivered and a similarity in the corresponding average particular delivery time. Based on results of the evaluating, aggregating average basal delivery dosages meeting a drug amount similarity threshold may be aggregated and a time range related to an aggregation of particular delivery times of the aggregated average basal delivery dosage may be assigned based on a time similarity threshold. The basal drug delivery schedule may be modified with an updated amount of the drug to be delivered as an updated basal delivery dosage based on the aggregated average basal delivery dosages, and an updated particular delivery time based on the assigned time range. The process may cause delivery of respective updated basal delivery dosages by the controller according to the modified basal drug delivery schedule via a pump mechanism communicatively coupled to the controller.

In another aspect, a process is disclosed that includes accessing, by a controller of a drug delivery device, a drug delivery history, a bolus drug history, a blood glucose measurement history, and a meal announcement history for a period of time from a memory coupled to the controller. The drug delivery history is a data structure containing drug amount data related to background doses of a drug delivered at respective times over the course of the drug delivery history based on an algorithm executed by the controller. The bolus drug history is a data structure containing bolus delivery time data related to delivery of bolus doses of the drug and an amount of the drug delivered in each bolus dose of the bolus doses. The blood glucose measurement history is a data structure of blood glucose measurement values in which each blood glucose measurement value has a corresponding time when the blood glucose measurement value was obtained. The meal announcement history is a data structure of times when a meal announcement notification was received by the controller. Respective data in each of the drug delivery history, the bolus drug history, the blood glucose measurement history, and the meal announcement history may be filtered by the controller according to predetermined filter settings related to a time interval of the period of time. A daily basal profile may be calculated using the filtered respective data from each of the drug delivery history, the bolus drug history, the blood glucose measurement history, and the meal announcement history. The daily basal profile may be a time schedule for delivering respective basal delivery dosages that includes times at which a basal delivery dosage of the respective basal delivery dosages is to be delivered. A control signal for delivery of a basal dosage of the calculated basal delivery dosages at a scheduled time from the daily basal profile may be generated by the controller. The control signal may be output to a pump mechanism of the drug delivery device communicatively coupled to the controller causing delivery of a respective basal dosage in the daily basal profile.

In a further aspect, a drug delivery device is disclosed that includes a controller, a pump mechanism, and a memory. The memory coupled to the controller and configured to store a drug delivery history and instructions. The controller, when executing the instructions, is configured to retrieve the drug delivery history that is a collection of basal drug delivery dosages delivered according to a basal drug delivery schedule from the memory. The drug delivery history may include a predetermined number of basal drug delivery dosages of a drug delivered over a period of time. The period of time may be further partitioned into intervals that span a time range less than the period of time. The drug delivery schedule may include a particular delivery time for each basal drug delivery dosage in the collection during each respective interval, and each basal drug delivery dosage in the collection is an amount of the drug delivered at the particular delivery time during each respective interval and each particular delivery time is one point in time during the interval. The method also includes processing, by the controller, the basal drug delivery dosages in the period of time to remove short term fluctuations of the basal drug delivery dosages over the period of time. The method also includes evaluating the processed basal drug delivery dosages within each interval to obtain an interval profile for each of the intervals within the period of time, where the interval profile is a data structure including the amount of the drug delivered in each processed basal drug delivery dosage and the particular delivery time associated with each processed basal drug delivery dosage during the interval. In the method, each processed basal drug delivery dosage may be analyzed at each particular delivery time in each interval profile for an interval and for every interval during the period of time. From the analysis, an average interval profile may be determined. The average interval profile may contain a series of average basal drug delivery dosages where each average basal drug delivery dosage in the series has a corresponding average particular delivery time. The controller may iteratively evaluate each average basal drug delivery dosage in the series with respect to other average basal drug delivery dosages in the series to determine a similarity in the amount of drug delivered and a similarity in the corresponding average particular delivery time. Based on results of the iterative evaluating, aggregating average basal delivery dosages meeting a drug amount similarity threshold may be aggregated and a time range related to an aggregation of particular delivery times of the aggregated average basal delivery dosage may be assigned based on a time similarity threshold. The basal drug delivery schedule may be modified with an updated amount of the drug to be delivered as an updated basal delivery dosage based on the aggregated average basal delivery dosages, and an updated particular delivery time based on the assigned time range. The process may cause delivery of respective updated basal delivery dosages by the controller according to the modified basal drug delivery schedule via a pump mechanism communicatively coupled to the controller.

In another aspect, a drug delivery device is disclosed that may include a controller; a pump mechanism communicatively coupled to the controller, and a memory coupled to the controller. The memory may be configured to store a drug delivery history and instructions that, when executed by the controller, configure the drug delivery device to obtain from the drug delivery history stored in the memory, basal drug dosage data. The obtained basal drug dosage data may include information related to a plurality of basal dosages delivered daily over a number of weeks. The controller may process the obtained basal dosage data using a low pass filter. From the processed basal dosage data, a daily basal profile may be generated that includes a number of basal dosages and a respective time for each of the basal dosages of the number of basal dosages to be delivered during a day. A control signal may be generated according to the daily basal profile. The control signal may be applied to the pump mechanism to deliver a respective basal dosage at the basal dosages respective time in the daily basal profile.

BRIEF DESCRIPTION OF THE DRAWINGS

To easily identify the discussion of any particular element or act, the most significant digit or digits in a reference number refer to the figure number in which that element is first introduced.

4

Figure 3:
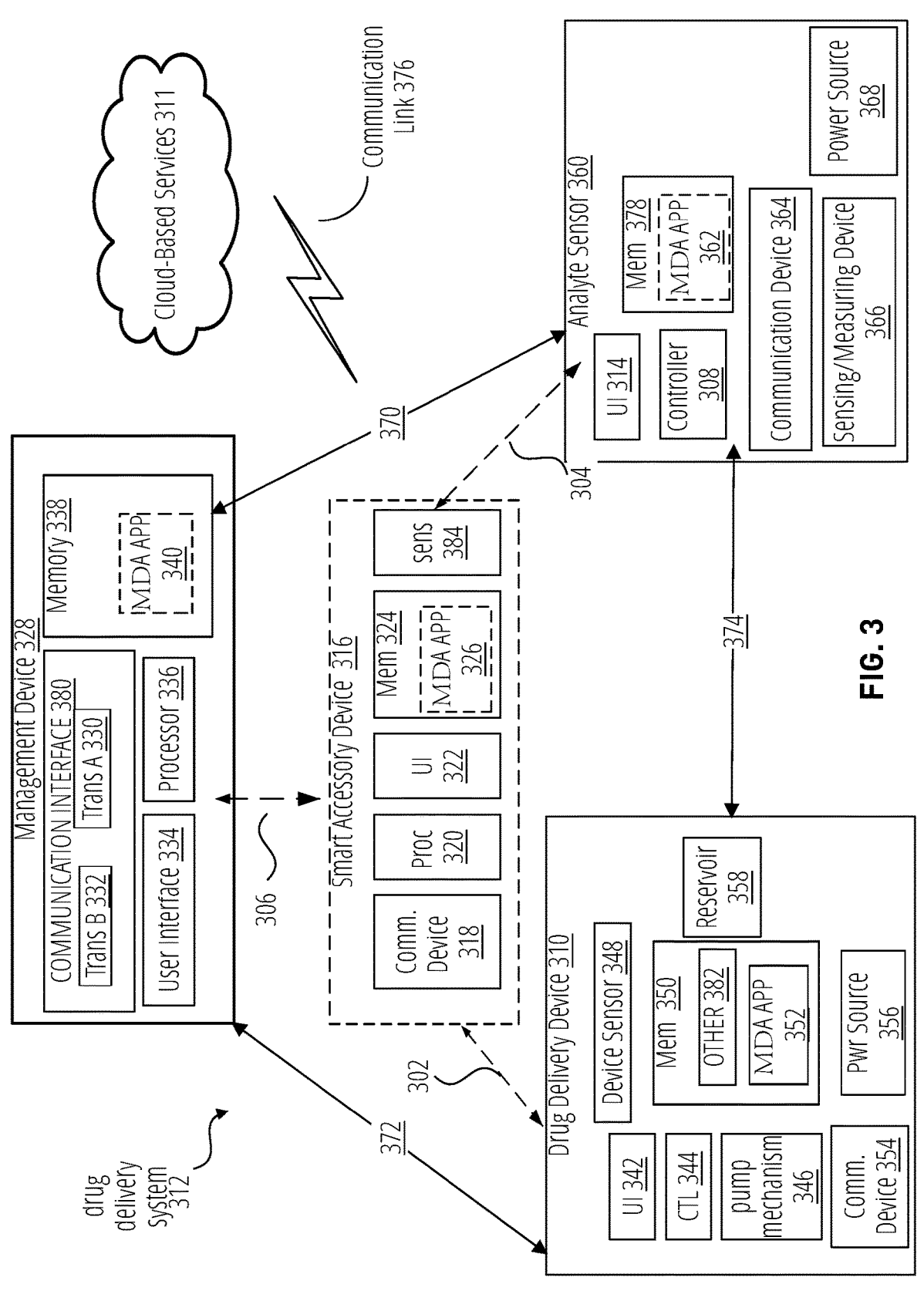

FIGS. 1A and 1B illustrate an example routine utilizing minimal data related to delivery of a drug by a drug delivery device.

FIG. 2 illustrates another example routine utilizing multiple different sets of data related to delivery of a drug by a drug delivery device.

FIG. 3 illustrates an example system suitable for implementing the example routines of FIGS. 1A-2 as well as other example routines or processes in accordance with the disclosed embodiments.

DETAILED DESCRIPTION

Systems, devices, computer-readable medium and methods in accordance with the present disclosure will now be described more fully hereinafter with reference to the accompanying drawings, where one or more embodiments are shown. The systems, devices, and methods may be embodied in many different forms and are not to be construed as being limited to the embodiments set forth herein. Instead, these embodiments are provided so the disclosure will be thorough and complete, and will fully convey the scope of methods and devices to those skilled in the art. Each of the systems, devices, and methods disclosed herein provides one or more advantages over conventional systems, components, and methods.

Various examples provide a method, a system, a device and a computer-readable medium for responding to inputs provided by sensors, such as an analyte sensor, and users of an automatic drug delivery system. The various devices and sensors that may be used to implement some specific examples may also be used to implement different therapeutic regimens using different drugs than described in the specific examples.

In one example, the disclosed methods, system, devices or computer-readable medium may perform actions related to managing a user's blood glucose in response to ingestion of a meal by the user.

The disclosed examples provide techniques that may be used with any additional algorithms or computer applications that manage blood glucose levels and insulin therapy. These algorithms and computer applications may be collectively referred to as "medication delivery algorithms" or "medication delivery applications" and may be operable to deliver different categories of drugs (or medications), such as chemotherapy drugs, pain relief drugs, diabetes treatment drugs (e.g., insulin), blood pressure medication, hormones or the like.

A type of medication delivery algorithm (MDA APP) may include an "artificial pancreas" algorithm-based system, or more generally, an artificial pancreas (AP) application. For ease of discussion, the computer programs and computer applications that implement the medication delivery algorithms or applications may be referred to herein as an "MDA application." An AP application may be configured to provide automatic delivery of insulin based on a blood glucose sensor input, such as signals received from an analyte sensor, such as a continuous blood glucose monitor, or the like. In an example, the artificial pancreas (AP) application when executed by a processor may enable monitoring of a user's blood glucose measurement values, determine an appropriate level of insulin for the user based on the monitored glucose values (e.g., blood glucose concentrations or blood glucose measurement values) and other information, such as information related to, for example, carbohydrate intake, exercise times, meal times or the like, and take actions to maintain a user's blood glucose value within an appropriate range. A target blood glucose value of the particular user may alternatively be a range blood glucose measurement values that are appropriate for the particular user. For example, a target blood glucose measurement value may be acceptable if it falls within the range of 80 mg/dL to 120 mg/dL, which is a range satisfying the clinical standard of care for treatment of diabetes. In addition, an AP application as described herein determine when a user's blood glucose wanders into the hypoglycemic range or the hyperglycemic range.

As described in more detail with reference to the examples of FIGS. 1A-2, an automatic drug delivery system may be configured to implement a method to estimate and update the time-dependent basal profile for a user after a certain period of closed loop operation time (e.g., 14 days). The first example as illustrated in FIGS. 1A and 1B may only utilize the history of insulin delivered by an AID algorithm. The described processes may be suitable for users who manage their blood glucose within acceptable range (e.g., approximately 0%-15%) of their target blood glucose setting most of the time (e.g., approximately 85%-100%) and bolus their meals accurately most of the time (e.g., approximately 85%-100%). The second example described with reference to FIG. 2 utilizes all insulin, CGM, and meal information, and tries to compensate for non-ideal meal boluses. The second example may be implemented when the fasting blood glucose measurement values being persistently high/low, and the delivered boluses either over/under compensate for meals, in which case the basal delivery dosages are likely to be underestimated or overestimated.

The routine 100 may process the drug delivery history maintained over the certain period of closed loop operation time, which is referred to as a period of time that is maintained as the drug delivery history. This drug delivery history may be stored in a permanent, non-disposable device that may communicate with a disposable pump, such as a personal diabetes management (PDM) device or be stored on the cloud and downloaded to be utilized in the embodiments within this application. The drug delivery history may, for example, include a predetermined number of basal drug delivery dosages of a drug delivered over a period of time. In the examples, the drug delivery history may be a collection of basal drug delivery dosages delivered according to a basal drug delivery schedule. The schedule may, for example, include a particular delivery time for each basal drug delivery dosage in the collection during each respective interval (e.g., deliveries every hour, 60 minutes, 30 minutes, or the like).

In the examples, a period of time may be a month, a number of months, week, or a number of weeks less than or longer than a month, a day, a number of days, a number of hours, such as 72, 84 or 96, or the like. In routine 100, the period of time may be further partitioned into a number of intervals and each interval may span a time range less than the period of time. For example, an interval may be a day, a week, a certain number of days, such as 3, 5, a certain number of hours, such as 6, 12, 24, 36, 72 or the like, or another interval of time, which is less than the period of time. A day equals 24 hours in these examples. For example, the period of time may be two weeks, the interval may be a day, and the day may be further segmented into respective times, such as 2 hour increments. In addition, each basal drug delivery dosage in the collection may be an amount of the drug delivered at the particular delivery time during each respective interval and each particular delivery time is one point in time during the interval. The particular delivery time may correspond to a respective time (t).

In block 102, a controller on a wearable drug delivery device, when implementing routine 100, may be configured and operable to retrieve the drug delivery history from a memory coupled to the controller. The controller and memory are shown in another example.

In block 104, routine 100 enables the controller to process the basal drug delivery dosages from the drug delivery history in the period of time to remove short term fluctuations of the basal drug delivery dosages over the period of time. For example, a low pass filter with a cutoff frequency of 0.14 mHz (1 cycle/2 hours) may be applied to the data a(t) from the drug delivery history to eliminate discrepancies or outliers in the data. The respective basal drug delivery history may be divided into 14 24-hour (1-day) intervals and processed by the controller using the low pass filter.

In block 106, routine 100 evaluates the respective processed basal drug delivery dosages within each interval to obtain an interval profile for each of the intervals within the period of time. The interval profile may, for example, be a data structure with a number of entries that includes for each entry, an amount of the drug delivered in each processed basal drug delivery dosage and the particular delivery time associated with each processed basal drug delivery dosage during the interval.

In some examples, an average basal drug delivery dosage for each particular time within the drug delivery history. For example, each particular basal drug delivery dosage delivered at the particular delivery time within each interval in the period of time may be averaged to obtain the estimate of a daily basal profile. In the example, the filtering cutoff frequency of (1 cycle/2 hours) reduces the 24 hours of the period of time into 12 2-hour intervals, which may be referred to as basal profile intervals. Each of the 12 individual basal profile intervals that are identified based on the processed data from the drug delivery history may be include an amount of a drug delivered via the basal dosage during that interval, basal profile intervals with defined amounts of the drug within a certain threshold (such as 0.05 U~0.25 U) may be clustered to provide a smaller number of intervals (e.g., 3 4-hour intervals) in the daily basal profile that can be more easily utilized by the users for their personal diabetes treatment applications.

In an example where the period of time is 1 week, and the interval may be 1 day. Each 1-day interval may be further segmented into times (t), which may be increments of 1 hour, 2 hours, 5, 10, 20 or 30 minutes or the like. In one example, the daily basal profile may initially contain the average basal delivery for each 2 hour period within a given day, in which case the time (t) increments are 2 hours.

In block 108, the controller while executing routine 100 may analyze each processed basal drug delivery dosage at each particular delivery time in each interval profile for an interval and for every interval during the period of time. For example, a basal dosage of a drug may be administered every 5 minutes over the course of an interval (e.g., a day, 24 hours, 12 hours or the like). The amount of the basal dosage (e.g., 0.5 Units of insulin, glucagon, glucagon-like peptide, or another drug or hormone) and the time of delivery (e.g., 0600) may be stored. The intervals, such as days, may be differentiated in a memory of a wearable drug delivery device based on an activation time of the wearable drug delivery device. For example, the wearable drug delivery device may have a clock or a counter that starts at the activation time, which may be at 8 am on the first day.

In block 110, routine 100 determines, from the analysis, an average interval profile, which contains a series of average basal drug delivery dosages, wherein each average basal drug delivery dosage in the series has a corresponding average particular delivery time. The average basal drug delivery dosages may be the average amount of the drug delivered as a basal dosage at a particular time (e.g., a time t, such as 7 AM during an interval (e.g., 24 hour period-1 day)) over the entire drug delivery history. For example, due to the filtering, the 24 hour period of the interval may be segmented into 12 particular times that are separated by 2 hours (e.g., the particular time t=1 may be 7 am, the particular time t=2 would be 9 am, and the particular time t=3 would be 11 am, and so on). The average delivery dosage for particular time between t=1 and t=2 in each interval may be 0.05 U, the average delivery dosage for particular time between t=2 and t=3 in each interval may also be 0.05 U, while average delivery dosage for the particular time between t=3 to the end of the day in each interval may be 0.25 U.

In block 112, the controller when implementing routine 100 may be configured to evaluate, iteratively, each average basal drug delivery dosage in the series of average basal drug delivery dosages with respect to other average basal drug delivery dosages delivered at different times in the series to determine a similarity in the amount of drug delivered and a similarity in the corresponding average particular delivery time. Continuing with the numerical example, the controller may determine the similarity in the amount of drug delivered at particular times t=1 and t=2 is 1.0 while the similarity in the amount of drug delivered at times t=2 and t=3 is 0.20 or the like. The similarity of each delivery between segments can be compared by evaluating the % change in amount of drug delivery. For instance, in the numerical example, the change in drug delivery from 1.0 between t=1 and t=2, versus 0.2 from t=2 and t=3, where the % change is 0.2/1.0=20%, and thus the "similarity" is −20%. The routine 100 continues to FIG. 1B.

In FIG. 1B, the controller may be further configured when executing the routine 100 may, in block 114, based on results of the evaluating, aggregate the average basal delivery dosages that meet a drug amount similarity threshold. The average drug similarity threshold may be based on a percentage of the average amounts being compared, such as within 5%, 10% or the like. In addition, a time range related to an aggregation of particular delivery times of the aggregated average basal delivery dosage may be assigned based on the time similarity threshold. The time similarity threshold may also be a percentage of the segmented time. For example, if the time segment is 2 hours (120 minutes), the time threshold may be 5%, 10% or the like, which means the time similarity threshold may be 6 minutes, 12 minutes or the like. This aggregated average basal delivery dosage, in an example, may be a sum of an amount of the drug delivered at the first corresponding average particular delivery time and an amount of the drug delivered at the second corresponding average particular delivery time based on the time threshold. Alternatively, the controller may use a clustering algorithm on the average basal delivery dosages that are close in range of a respective drug amount similarity threshold and a time delivery threshold.

In an example, the controller may be configured to combine a first average basal delivery dosage from a first corresponding average particular delivery time (e.g., between t=1 and t=2) with a second average basal delivery dosage from a second corresponding average particular delivery time (e.g., between t=2 and t=3). The combining of the first average basal delivery dosage and the second average basal delivery dosage provides the updated basal delivery dosage. For example, the average basal dosages of 0.05 U at particular time between t=1 and t=2—as well as between t=2 and t=3 may be aggregated as 0.10 U between t=1 and t=3. In addition, the controller may be further configured to combine the first average particular delivery time with the second average particular delivery time. For example, the particular time may be aggregated to provide an aggregate time of 4 hours. This results in an aggregate average delivery dosage of 0.1 U over 4 hours in this numerical example.

In block 116, the controller may modify the basal drug delivery schedule with: an updated amount of the drug to be delivered as an updated basal delivery dosage based on the aggregated average basal delivery dosages, and an updated particular delivery time based on the assigned time range. In addition, the controller may set, for a new interval for which the modified basal drug delivery schedule is to be applied, a start time of the updated basal delivery dosage that corresponds to the updated particular delivery time.

The controller, at block 118, may cause delivery of respective updated basal delivery dosages according to the modified basal drug delivery schedule via a pump mechanism (shown in another example) communicatively coupled to the controller. For example, the controller may generate an activation control signal at the start time in a new interval to expel the updated basal delivery dosage from a drug container. The new interval being a day in the modified basal drug delivery schedule. The generated activation signal may be output to a pump mechanism coupled to the drug container and the controller (as described with reference to FIG. 3).

The example routine 100 is implemented utilizing data from the drug delivery history alone because of the consistent blood glucose measurement values of the particular individual. However, other individuals that may need more flexibility may rely on an algorithm that inputs additional data when determining an adjusted basal need.

FIG. 2 illustrates a routine 200 in accordance with another example of the disclosed subject matter. The routine 200 provides additional robustness by utilizing data from different histories of the user.

In block 202, a controller of a drug delivery device when executing programming code that implements routine 200 may be configured to access in a memory coupled to the controller a drug delivery history, a bolus drug history, a blood glucose measurement history, and a meal announcement history for a period of time.

In the example of routine 200, the drug delivery history may be a data structure containing drug amount data related to background (or basal) doses of a drug delivered at respective times over the course of the drug delivery history based on an algorithm executed by the controller. For example, the drug amount data may be related to insulin or glucagon, and may be in units of insulin, such as 0.5 Units (U), 0.25 U, 0.05 U or the like, and a time of the delivery may be stored as a respective time for each delivery, such as 0500 (5 am), 0346 (5:25 am), 0700 (7 am), 1345 (1:45 pm), 1900 (7 pm) or the like. Of course, other drugs, such as methadone, morphine, or the like, may be administered. Since the drug delivery history tracks background or basal doses deliveries of the drug, the drug delivery history may have multiple deliveries (e.g., 1-20 instances) and relatively small amounts of the drug (in comparison to the bolus dosages) delivered (e.g., 0.5 U versus 30.0 U) per each instance throughout an interval.

The bolus drug history may, for example, be a data structure containing bolus delivery time data related to delivery of bolus doses of the drug and an amount of the drug delivered in each bolus dose of the bolus doses. For example, the bolus drug history may be arranged similar to the drug delivery history and may have an amount of the drug delivered. In addition, the blood glucose measurement history may, for example, be a data structure of blood glucose measurement values (blood glucose measurement values) in which each blood glucose measurement value has a corresponding time when the blood glucose measurement value was obtained. For example, the data structure may have a blood glucose measurement value in one column, such as 120 mg/dL, and in another column a time, such as 0600 (6 am), or the like.

In some examples, the controller may access the meal announcement history, which, for example, —may be a data structure of times when a meal announcement notification was received by the controller. In some examples, the meal announcement notification may be received from a user interface device, such as a switch, push button, keyboard, touchscreen display, a microphone, or the like. The controller may, for example, store the meal announcement notification with a time that the notification was received, for example, the meal announcement notification may be a binary indication, such as Yes or No, or some other type of flag, and the time associated with the meal announcement notification may be a time, such as 0600 (6 am), 1200 (12 pm) and 1800 (6 pm), or the like. At a time when a meal announcement is not received, the controller may set the indication to No and log the time which corresponds to other times stored in the other data structures for the drug delivery history, bolus drug history, and the blood glucose measurement history.

In block 204, the controller when executing routine 200 filters respective data in each of the drug delivery history, the bolus drug history, the blood glucose measurement history, and the meal announcement history, according to predetermined filter settings related to a time interval of the period of time. For example, a low pass filter with a cutoff frequency of approximately 0.14 millihertz (1 cycle/2 hours) may be applied to the respective data in each of the drug delivery history (which may be referred to as a(t)), the bolus drug history (which may be referred to as b(t)), the blood glucose measurement history (which may be referred to as g(t)), and the meal announcement history (which may be referred to as m(t)). The controller may be configured to divide the filtered data into 14 24-hour (1-day) periods. In other examples, the controller may cutoff frequencies other than 1 cycle/2 hours may be chosen, such as 1 cycle/3 hours or the like. Furthermore, the filters for the bolus drug history, the blood glucose measurement history, and the meal announcement history may be chosen with different shapes and durations to match the expected insulin/meal absorption curves, insulin-on-board (IOB)/carbohydrates-on-board (COB) curves, or the like.

In block 206, routine 200 calculates a daily basal profile using the filtered respective data from each of the drug delivery history, the bolus drug history, the blood glucose measurement history, and the meal announcement history. The daily basal profile may be, for example, a time schedule for delivering respective basal delivery dosages and times at which a basal delivery dosage of the respective basal delivery dosages is to be delivered. The respective basal delivery dosages and times in the daily basal profile may correspond to a respective adjusted basal need calculated for a respective time in the interval.

The example process at block 206 may include the controller determining a series of time settings for times in the time schedule based on the predetermined filter settings from block 204. For example, each time in the series of time settings may be selected based on the time interval (i.e., interval) of the period of time. The controller may access a memory to obtain an amount of the drug from the drug amount data in the drug delivery history a(t) and at a time (t) in the drug amount data that corresponds to each time in the series of time settings. The amount of the drug from time t may be referred to as a "drug delivery history factor" for the respective time t. The controller may further be configured to obtain, from the bolus drug history b(t), a respective amount of the drug delivered in a bolus dose at each time (t) in the series of time settings. The controller may be further configured to determine a number of blood glucose measurement factors from blood glucose measurement values g(t) in the blood glucose measurement history and that corresponds to a respective time (t) in the series of time settings. Based on these calculated factors (i.e., drug delivery history factors, blood glucose measurement factors, the bolus history factor).

In block 208, routine 200 generates, by the controller, a control signal for delivery of a basal dosage of the calculated basal delivery dosages at a scheduled time from the daily basal profile.

In block 210, routine 200 causes the controller to output the control signal to a pump mechanism of the drug delivery device communicatively coupled to the controller.

In other examples, the calculation of the daily basal profile at block 206 may be performed using different processes. An adjusted basal need may be an individual entry in the daily basal profile. The adjusted basal need may, in one example, be obtained based on a number of different factors as discussed in the respective examples below.

In other examples, the controller may be configured to account for additional data that is collected based on the assumption that a user is not paying close attention to blood glucose measurement values in which case the adjusted basal need discussed above may be used in combination with other factors. The controller may determine the adjusted basal need according to different equations depending upon the example. The respective equations may utilize different factors, such as a drug delivery history factor obtained from the drug delivery history, a bolus drug factor obtained from the bolus drug history, a blood glucose measurement factor obtained from the blood glucose measurement history, and a meal announcement factor based on a meal announcement history. In other examples, a proportionality factor may be incorporated into the equation to further optimize the basal dosage settings.

For example, the drug delivery history factor may be an amount of basal drug delivered at a respective time t taken from the drug delivery history. The amounts of the basal drug delivered in the drug delivery history a(t).

In another example, the controller may be configured to determine a blood glucose measurement factor for each respective time (i.e., t) of a number of preselected times from the blood glucose history. For example, the controller may obtain, by accessing a memory, a blood glucose measurement value from the blood glucose measurement history stored in the memory that corresponds to the respective time (t). The controller, in the example, may use the respective time (t) in the following equation to determine the blood glucose measurement factor:

$$\frac{g(t) - 120}{DIA \cdot CF},$$ (Eq. 1)

where g(t) is the blood glucose measurement value from the blood glucose measurement history at the respective time (t), the value 120 is a fasting blood glucose target setting, DIA is the duration of insulin action (e.g., 3 hours or the like), and CF is the estimated correction factor (e.g., estimated using the rule 1800/TDI).

In evaluating Equation 1, the controller may determine a numerator, specific to the respective time (t) of the preselected times, by subtracting the fasting blood glucose target setting from the obtained blood glucose measurement value g(t) corresponding to the respective time. The denominator may be determined by multiplying a duration of insulin action (DIA) value by an estimated correction factor. The denominator may remain constant over the period of time, such as two weeks, but may be updated based on changes to a user's physical attributes (e.g., the consistency of blood glucose measurement value) or habits (e.g., diet or physical activity).

In Equation 1, the estimated correction factor CF may be an estimate of a specific user's sensitivity to insulin (or glucagon) and how efficiently the user processes the insulin (or glucagon). The fasting blood glucose target setting in this example is 120, but different values may also be used, such as 115 mg/dL, 130 mg/dL, 140 mg/dL or the like. In some examples, the fasting blood glucose target setting may be user dependent. For example, the controller may obtain the fasting blood glucose target setting from user preference settings (described with reference to a later example) or from a clinical setting common for the physical attributes (e.g., height, weight, age, resting heart rate and/or the like) of the user that are stored in the memory accessible by the controller. Alternatively, it may be obtained from clinical data sources and input into the memory coupled to the controller.

For example, the controller may determine individual adjusted basal need for each respective time (t) in the daily basal profile based on the blood glucose measurement factor that corresponds to each time in the series of time settings may be calculated, for example, using the obtained blood glucose measurement value (g(t)), a fasting blood glucose target setting (e.g., 120), a duration of insulin action value (DIA), and a correction factor (CF).

In addition, the controller may also determine a meal announcement factor that corresponds to each time in the series of time settings based on the meal announcement history. The controller may also determine a drug ratio related to meal content in which the drug ratio related to meal content may be an insulin-to-carbohydrate ratio. The meal announcement factor may be determined by retrieving a meal announcement value corresponding to a respective time in the series of time settings. In the example, the meal announcement value may be an estimate of a number of grams of carbohydrates in the meal that triggered a particular meal announcement notification. A meal announcement notification may be received via user input, an automatic meal detection algorithm, historical data or the like. For example, the estimated number of grams of carbohydrates may be input by the user via a user interface to a drug delivery device. Alternatively, the estimated number of carbohydrates may be determined by a meal detection algorithm that utilized historical data of changes in blood glucose measurement values to generate a meal announcement notification. In another alternative, a meal detection algorithm may utilize inputs from various sensors (e.g., camera or microphone, global positioning sensors) and computer applications (e.g., calendar applications, travel direction applications, recipe applications, or the like).

Based on one or more of the meal detection or meal announcement processes, the controller may determine or estimate an insulin-to-carbohydrate ratio. The controller may use the insulin-to-carbohydrate ratio (IC) as the divisor in a division operation in which the numerator is the meal announcement value by the, the quotient of the division may be referred to as the meal announcement factor. For example, an equation (Eq. 2) for the meal announcement factor may be:

$$\frac{m(t)}{IC} \tag{Eq. 2}$$

where m(t) is the meal announcement value and IC is the insulin-to-carbohydrate ratio.

In these more detailed calculations, the adjusted basal need of routine 100 may have been calculated utilizing only the obtained amount of the drug from the drug delivery history a(t). However, as more factors are used in the routine 200, the controller may, for example, determine "an aggregate factor." The controller may be configured to sum the obtained amount of the drug from the drug delivery history a(t) from the drug amount data in the drug delivery history, the respective blood glucose measurement factor, and the obtained respective amount of the drug delivered in the bolus dose to provide the aggregate factor. The aggregate factor, in this example, for a respective time (t) may generally refer to the sum of values from the respective time (t) in the drug delivery history and the bolus drug history, and the blood glucose measurement factor based on the respective time (t). For example:

$$\text{Aggregate Factor}(t) = a(t) + \frac{g(t) - 120}{DIA \cdot CF} + b(t) \tag{Eq. 3}$$

where t is a respective time, a(t) is the obtained amount of the drug from the drug amount data delivered via basal dosages in the drug delivery history at the respective time, and the term:

$$\frac{g(t) - 120}{DIA \cdot CF}$$

in the aggregate factor(t) may be, as mentioned above, the "blood glucose measurement factor" at the respective time (t).

In an alternative example, during the steps of block 206, the controller may be configured to determine the number of blood glucose measurement factors from the blood glucose measurement history using different techniques in different examples. In the specific example, the controller may be operable to calculate an adjusted basal need for each respective time (t) in the daily basal profile using the following equation (Eq. 4):

$$\text{Adjusted Basal Need } [a_{adj}(t)] = \text{Drug Delivery History Factor } [a(t)] +$$
$$\text{Blood Glucose Measurement Factor } \left[\frac{g(t) - 120}{DIA \cdot CF}\right] +$$
$$\text{Bolus History Factor } [b(t)] - \text{Meal Announcement Factor } \left[\frac{m(t)}{IC}\right]$$

where (t) is a preselected time of the interval with the interval set as 24 hours or 1 day, the drug delivery history factor, blood glucose measurement factor and bolus history factor are collectively referred to as the "aggregate factor" explained above, the meal announcement factor is based on an estimated grams (as referred to as "number") of carbohydrates in a meal that triggered a meal announcement m(t) at respective time (t), and IC is the estimated insulin-to-carbohydrate ratio (e.g., estimated using the rule 800/TDI).

In the example, each calculated adjusted basal need may be an individual entry in the schedule. For example, the controller may be configured, for each respective time of the plurality of preselected times, to provide an aggregate factor, which is a sum of the obtained amount of the drug at the respective time, the obtained respective amount of the drug delivered in the bolus dose, and the respective blood glucose measurement factor. The controller is further configured to subtract from the aggregate factor the meal announcement factor from the respective time and output the result of the summing and subtracting as the adjusted basal need for a respective time (t) of the plurality of preselected times.

In yet another example of calculating the adjusted basal need for the time schedule of the daily basal profile as part of the processing at block 206, the adjusted basal need for a respective time of the number of preselected times may be determined using another process that accounts for the user's correction bolus $b_c(t)$ at respective time t that may be associated with meal ingestions depending on the user's use cases. The drug delivery device may be manually commanded by the user to deliver the correction bolus. Alternatively, or in addition, the controller may, based on user preference settings, be permitted to deliver the correction bolus. In one exemplary embodiment, correction boluses $b_c(t)$ can also be processed with a low pass filter having a cutoff frequency of approximately 0.14 mHz or another cutoff frequency setting. A proportion X of these manual correction bolus $b_c(t)$ may be considered to be relevant to meals and subtracted to address the user's basal needs with further specificity.

For example, the controller may be configured to determine the adjusted basal need for each respective time of the number of preselected times, based on the following (Eq. 5):

$$a_{adj}(t) = a(t) + \frac{g(t) - 120}{DIA \cdot CF} + b(t) - \frac{m(t)}{IC} - X \cdot b_c(t) \qquad \text{(Eq. 5)}$$

where (t) is a preselected time of the interval with the interval set as 24 hours or 1 day, the value 120 is an example of the target fasting blood glucose setting (which may be different for different users), DIA is the duration of insulin action (e.g. 3 hours), CF is the estimated correction factor (e.g. 1800/TDI), IC is the estimated insulin-to-carb ratio (e.g. 800/TDI), $b_c(t)$ is the correction bolus of the user and the X may be a proportionality factor.

In one example, the proportionality factor X may be considered 0.5, which is an assumption that half of the manual boluses used by the examiner over the course of the interval may be associated with meals (e.g., the user manually attempting to compensate for meal consumption). Of course, values other than 0.5 may be set for the proportionality factor X, such as 0.3, 0.55, or the like. Users who exhibit keto diets may assume a lower proportionality factor than 0.5, as they may not need significant insulin associated with meals. Users who are highly active may not need as much insulin associated with basal delivery and may assume a higher proportionality factor than 0.5. This value can be potentially fixed to an individualized value per user and per recommendation from the physician, adjusted occasionally by the user and the physician manually every fixed period of time, such as 3-14 days, or adjusted automatically based on the proportion of insulin delivery as basal versus bolus in the available drug delivery history every fixed period of time.

In yet another example, rather than subtracting the insulin deliveries from the aggregate factor as described in the equations above, the summation of all insulin deliveries can be adjusted by a proportion of bolus insulin deliveries versus the automated insulin deliveries. Allowances may be made to more heavily bias towards an equal split between basal insulin delivery needs and bolus insulin delivery needs.

In this example, the controller may access a memory to obtain an amount of the drug from the drug amount data in the drug delivery history (a(t)) and at a time (t) (which is a respective time or may be the "time interval") in the drug amount data that corresponds to each time in the series of time settings. The controller may further be configured to obtain, from the bolus drug history (b(t)), a respective amount of the drug delivered in a bolus dose at each time (t) in the series of time settings. The controller may be further configured to determine a number of blood glucose measurement factors from blood glucose measurement values (g(t)) in the blood glucose measurement history and that corresponds to a respective time (t) in the series of time settings. Each respective blood glucose measurement factor (g(t)) of the number of blood glucose measurement factors may correspond to a respective time (t) in the series of time settings. The controller may be further configured to calculate a blood glucose measurement factor that corresponds to each time in the series of time settings using the obtained blood glucose measurement value, a fasting blood glucose target setting, a duration of insulin action (DIA) value, and an estimated correction factor (CF). All of the factors below may be calculated as described with reference to the examples of FIGS. 1A-2 above.

In this specific example, the routine 200 may configure the controller, when determining the adjusted basal need for each of the number of preselected times, to summing the obtained amount of the drug, the respective blood glucose measurement factor, and the obtained respective amount of the drug delivered in the bolus dose to provide an aggregate factor. The controller may determine a proportion of an amount of drug provided via bolus dosages to an amount provided via the aggregate factor. The proportion may be modified based on a contribution factor.

In more detail, the controller may implement the following equation, and based on a(t), b(t), and g(t), the total insulin $a_{tot}(t)$ may be calculated (in a manner similar to the aggregate factor above) as:

$$a_{tot}(t) = a(t) + \frac{g(t) - 120}{DIA \cdot CF} + b(t)$$

In an example, the amount of insulin delivery for basal needs (referred to as $a_b(t)$ (below)) can be estimated based on the proportion of bolus versus total insulin as:

$$a_b(t) = a_{tot}(t) \cdot (\text{contribution factor})$$

where the contribution factor may be a weighting factor that can range between approximately 0.25 to approximately 0.75, or approximately 0.0-approximately 1.0, depending on the overall proportion of the insulin delivery for boluses versus total delivery.

In more detail, the contribution factor may be determined:

$$\text{contribution factor}\,(t) = \left(0.25 + 0.5 \cdot \frac{b(t)}{a_{tot}(t)}\right)$$

The total insulin $a_{tot}(t)$ (referred to as "the aggregate factor" in earlier examples) may be multiplied by the modified proportion to determine a resultant. The controller may be configured to output the resultant of the multiplying of $a_{tot}(t)$ and contribution factor as the adjusted basal need for a respective time of the plurality of preselected times.

The foregoing examples described a daily basal profile or a time schedule. The respective daily basal profile or time schedule may be the same for every day of the week. However, it is further envisioned that the controller may be configured to evaluate more broadly than single day and modify basal based on day of week, or day of year, such as large meals on Friday night or Sunday morning; or intense exercise on Saturdays, for example.

It may be helpful to describe an example of a system that may be configured to implement the above described examples as well as additional examples.

FIG. 3 illustrates a functional block diagram of a system example suitable for implementing the example processes and techniques described herein.

The drug delivery system 312 may implement (and/or provide functionality for) a medication delivery algorithm, such as an artificial pancreas (AP) application, to govern or control automated delivery of a drug or medication, such as insulin, to a user (e.g., to maintain euglycemia—a normal level of glucose in the blood). The drug delivery system 312 may be an automated drug delivery system that may include a wearable automatic drug delivery device 310, an analyte sensor 360, and a management device (PDM) 328. The drug delivery system 312 may be an automatic drug delivery system that is configured to deliver a dosage of the drug without any user interaction, or in some examples, limited user interaction, such as depressing a button to announce ingestion of a meal or the like.

The system 312, in an optional example, may also include a smart accessory device 316, such as a smartwatch, a personal assistant device or the like, which may communicate with the other components of system 312 via either a wired or wireless communication links 302-306.

The management device 328 may be a computing device such as a smart phone, a tablet, a personal diabetes management device, a dedicated diabetes therapy management device, or the like. In an example, the management device (PDM) 328 may include a processor 336, a management device memory 338, a user interface 334, and a communication interface 380. The management device 328 may contain analog and/or digital circuitry that may be implemented as a processor 336 for executing processes based on programming code stored in the management device memory 338, such as the AP algorithm or application (APP) 340, to manage a user's blood glucose levels and for controlling the delivery of the drug, medication, or therapeutic agent according to a time schedule, basal drug profile, and the like as discussed above. The management device 328 may be used to initially set up, adjust settings, and/or control operation of the wearable automatic drug delivery device 310 and/or the analyte sensor 360 as well as the optional smart accessory device 316.

The processor 336 may also be configured to execute programming code stored in the management device memory 338, such as the MDA APP 340. The MDA APP 340 may be a computer application that is operable to deliver a drug based on information received from the analyte sensor 360, the cloud-based services 311 and/or the management device 328 or optional smart accessory device 316. The memory 338 may also store programming code to, for example, operate the user interface 334 (e.g., a touchscreen device, a camera or the like), the communication interface 380 and the like. The processor 336 when executing the MDA APP 340 may be configured to implement indications and notifications related to meal ingestion, blood glucose measurements, and the like. The user interface 334 may be under the control of the processor 336 and be configured to present a graphical user interface that enables the input of a meal announcement, adjust setting selections and the like as described above.

In a specific example, when the memory 338 stores an MDA APP, such as an artificial pancreas application, the processor 336 may also be configured to execute a diabetes treatment plan (which may be stored in the memory 338) that is managed by the MDA APP 340 stored in memory 338. In addition to the functions mentioned above, when the MDA APP 340 is an AP application, it may further provide functionality to enable the processor 336 to determine a basal dosage according to an adjusted basal need, a basal drug profile or the like as described with respect to the examples of FIGS. 1A-2. In addition, the MDA APP 340 provides functionality to enable the processor 336 to output signals to the wearable automatic drug delivery device 310 to deliver the basal drug dosages described with reference to the examples of FIGS. 1A-2.

The communication interface 380 may include one or more transceivers such as Transceiver A 330 and Transceiver B 332 and receivers or transmitters that operate according to one or more radio-frequency protocols. In the example, the transceivers 332 and 330 may be a cellular transceiver and a Bluetooth® transceiver, respectively. For example, the communication interface 380 may include a transceiver 332 or 330 configured to receive and transmit signals containing information usable by the MDA APP 340.

The drug delivery device 310, in the example system 312, may include a user interface 342, a controller 344, a pump mechanism 346, a communication device 354, a memory 350, a power source 356, device sensors 348, and a reservoir 358. The wearable automatic drug delivery device 310 may be configured to perform and execute the processes described in the examples of FIGS. 1A-2 without input from the management device 328 or the optional smart accessory device 316.

The controller 344 alone may implement the processes of FIGS. 1A, 1B and 2 to determine a daily basal profile or an adjusted basal need as described with respect to the other examples, based on an input from the analyte sensor 360. The controller 344 of the wearable automatic drug delivery device 310 may be operable to implement delivery of a drug to the user according to a diabetes treatment plan or other drug delivery regimen stored in the memory 350 as other programs 382 (Other). For example, the controller 344 may be operable to execute programming code and be configured when executing non-transitory programming code of a medication delivery application or algorithm, such as MDA APP 340 and other programs 382, to perform the functions that implement the example routines and processes described herein. In an operational example, the controller 344, when executing the programming code implementing MDA APP 340, may be configured to output a control signal causing actuation of the drive mechanism 346 (the drive mechanism 346 may also be referred to as a pump mechanism) to deliver time-dependent basal dosages or the like as described with reference to the examples of FIGS. 1A-2.

The memory 350 may store programming code executable by the controller 344. The programming code, for example, may enable the controller 344 to control expelling insulin from the reservoir 358 and control the administering of doses of medication based on signals from the MDA APP 352 or, external devices, when the drug delivery device 310 is configured to receive and respond to the external control signals. The memory 350 may also be configured to store other data and programming code, such as other programs 382. For example, the memory may be configured to store the data structures discussed above with respect to the examples of FIGS. 1A-2 with data, such as the drug delivery history, bolus drug history, a blood glucose measurement history and a meal announcement history, a correction bolus history as well as data related to the time-dependent basal dosages, such as a daily basal profile, or a time schedule. In some instances, all glucose and insulin histories are stored in the management device 328, which may be a smartphone, or smart accessory 307, and the cloud-based services 311, which may include data storage. The drug delivery device 310 and CGM upload their histories to the management device 328, when in communication. The management device 328, in turn uploads the histories to the cloud-based services 311 periodically. When the drug delivery device 310 or analyte sensor 360 is disposed of, no history will be lost because the respective history is stored in the cloud by cloud-based services 311. Similarly, when a management device 328 or smart accessory 316 is replaced, no history will be lost. The basal profile adaptive computation as discussed in the example routines 1 and 2 may be performed on the management device 328 and transmitted to the drug delivery device 310 at activation of the drug delivery device 310 via a communication link, such as 372 or 302. Alternatively, the computation can be done in the cloud, downloaded to the management device 328, and then transmitted to the pod when activated.

The reservoir 358 may be configured to store drugs, medications or therapeutic agents suitable for automated delivery, such as insulin, morphine, blood pressure medicines, chemotherapy drugs, or the like.

The device sensors 348 may include one or more of a pressure sensor, a power sensor, or the like that are communicatively coupled to the controller 344 and provide various signals. In an example, the controller 344 or a processor, such as 336, may be operable to use the various signals in the determination of an amount of a drug delivered, a daily basal profile or an adjusted basal need as described with respect to the other examples. In such an example, the controller 344 may have a clock, a counter or the like that maintains or enables maintaining a time. An initial time may be set when the wearable drug delivery device is initially set up by a user or clinician.

In an example, the wearable automatic drug delivery device 310 includes a communication device 354, which may be a receiver, a transmitter, or a transceiver that operates according to one or more radio-frequency protocols, such as Bluetooth, Wi-Fi, a near-field communication standard, a cellular standard, or the like. The controller 344 may, for example, communicate with a personal diabetes management device 328 and an analyte sensor 360 via the communication device 354.

The wearable automatic drug delivery device 310 may be attached to the body of a user, such as a patient or diabetic, at an attachment location and may deliver according to an automatic drug delivery algorithm any therapeutic agent, including any drug or medicine, such as insulin or the like, to a user at or around the attachment location. A surface of the wearable automatic drug delivery device 310 may include an adhesive to facilitate attachment to the skin of a user as described in earlier examples. The controller 344 may be operable to maintain a drug delivery history of the delivered therapeutic drug, such as insulin, by storing delivered basal dosages and bolus dosages in memory 350. The memory 350 may also store a drug delivery history that may be a data structure containing drug amount data related to background doses of a drug delivered at respective times in the drug delivery history, a bolus drug history that may be a data structure containing bolus delivery time data related to delivery of bolus doses of the drug and an amount of the drug delivered in each bolus dose of the bolus doses, a blood glucose measurement history that may be a data structure of blood glucose measurement values in which each blood glucose measurement value has a corresponding time when the blood glucose measurement value was obtained, and a meal announcement history that may be a data structure of times when a meal announcement notification was received by the controller.

The wearable automatic drug delivery device 310 may, for example, include a reservoir 358 for storing the drug (such as insulin), a needle or cannula (not shown in this example) for delivering the drug into the body of the user (which may be done subcutaneously, intraperitoneally, or intravenously), and a drive mechanism 346 for transferring the drug from the reservoir 358 through a needle or cannula and into the user. The drive mechanism 346 may be fluidly coupled to reservoir 358, and communicatively coupled to the controller 344.

The wearable automatic drug delivery device 310 may further include a power source 356, such as a battery, a piezoelectric device, other forms of energy harvesting devices, or the like, for supplying electrical power to the drive mechanism 346 and/or other components (such as the controller 344, memory 350, and the communication device 354) of the wearable automatic drug delivery device 310.

In some examples, the wearable automatic drug delivery device 310 and/or the management device 328 may include a user interface 334, respectively, such as a keypad, a touchscreen display, levers, light-emitting diodes, buttons on a housing of the management device 328, a microphone, a camera, a speaker, a display, or the like, that is configured to allow a user to enter information and allow the management device 328 to output information for presentation to the user (e.g., alarm signals or the like). The user interface 334 may provide inputs, such as a voice input, a gesture (e.g., hand or facial) input to a camera, swipes to a touchscreen, or the like, to processor 336 which the programming code interprets.

When configured to communicate to an external device, such as the PDM 328 or the analyte sensor 360, the wearable automatic drug delivery device 310 may receive signals over the wired or wireless link 372 from the management device 328 or 374 from the analyte sensor 360. The controller 344 of the wearable automatic drug delivery device 310 may receive and process the signals from the respective external devices (e.g., cloud-based services 311, smart accessory device 316, or management device 328) to implement delivery of a drug to the user according to a daily basal profile, a time schedule, a modified basal drug delivery schedule stored in the memory 350 as other programs 382 (Other).

In an operational example, the controller 344 when executing the MDA APP 340 may output a control signal operable to actuate the drive mechanism 346 to deliver a carbohydrate-compensation dosage of insulin, a correction bolus, a revised basal dosage or the like as described with reference to the examples of FIGS. 1A-2.

The smart accessory device 316 may be, for example, an Apple Watch®, other wearable smart device, including eyeglasses, provided by other manufacturers, a global positioning system-enabled wearable, a wearable fitness device, smart clothing, or the like. Similar to the management device 328, the smart accessory device 316 may also be configured to perform various functions including controlling the wearable automatic drug delivery device 310. For example, the smart accessory device 316 may include a communication device 318, a processor 320, a user interface 322, a sensor 384, and a memory 324. The user interface 322 may be a graphical user interface presented on a touchscreen display of the smart accessory device 316. The sensor 384 may include a heart rate sensor, a blood oxygen saturation sensor, a pedometer, a gyroscope, a combination of these sensors, or the like. The memory 324 may store programming code to operate different functions of the smart accessory device 316 as well as an instance of the MDA APP 326. The processor 320 that may execute programming code, such as the MDA APP 326 for controlling the wearable automatic drug delivery device 310 to implement the FIG. 1A-2 examples described herein.

In an operational example, the drug delivery device 310 may be configured, when the controller 344 executes programming code stored in the memory, such as other programs 382 and MDA APP 352, to obtain from the drug delivery history stored in the memory, basal drug dosage data. The obtained basal drug dosage data obtained from the drug delivery history may include information related to a plurality of basal dosages delivered daily over a number of weeks. The controller may process the obtained basal dosage data using a low pass filter to reduce any outlier data points that may skew an average of the amounts of a drug delivered during a basal dosage. For example, the controller may be further configured to identify basal dosages within a same day of the processed basal dosage data that have similar drug amounts delivered in a basal dosage; and aggregate the identified basal dosages to reduce a number of different basal dosages to be accounted for in the daily basal profile. The drug delivery device may generate from the processed basal dosage data, a daily basal profile that includes a number of basal dosages and a respective time for each of the basal dosages of the number of basal dosages to be delivered during a day. The controller may generate a control signal according to the daily basal profile. The controller may apply the control signal to the pump mechanism to deliver a respective basal dosage at the basal dosages respective time in the daily basal profile.

In addition to the above operational example, the controller 344 may be operable or configured to execute programming code embodying the routine 100 of FIGS. 1A and 1B and routine 200 of FIG. 2.

The analyte sensor 360 may include a controller 308, a memory 378, a sensing/measuring device 366, a user interface 314, a power source/energy harvesting circuitry 368, and a communication device 364. The analyte sensor 360 may be communicatively coupled to the processor 336 of the management device 328 or controller 344 of the wearable automatic drug delivery device 310. The memory 378 may be configured to store information and programming code, such as an instance of the MDA APP 362.

The analyte sensor 360 may be configured to detect multiple different analytes, such as lactate, ketones, uric acid, sodium, potassium, alcohol levels, hormone levels, or the like, and output results of the detections, such as measurement values or the like. The analyte sensor 360 may, in an example, be configured to measure a blood glucose value at a predetermined time interval, such as every 5 minutes, or the like. The communication device 364 of analyte sensor 360 may have circuitry that operates as a transceiver for communicating the measured blood glucose values to the management device 328 over a wireless link 370 or with wearable automatic drug delivery device 310 over the wireless communication link 374. While called an analyte sensor 360, the sensing/measuring device 366 of the analyte sensor 360 may include one or more additional sensing elements, such as a glucose measurement element a heart rate monitor, a pressure sensor, or the like. The controller 308 may include discrete, specialized logic and/or components, an application-specific integrated circuit, a microcontroller or processor that executes software instructions, firmware, programming instructions stored in memory (such as memory 378), or any combination thereof.

Similar to the controller 344, the controller 308 of the analyte sensor 360 may be operable to perform many functions. For example, the controller 308 may be configured by the programming code stored in the memory 378 to manage the collection and analysis of data detected the sensing and measuring device 366.

Although the analyte sensor 360 is depicted in FIG. 3 as separate from the wearable automatic drug delivery device 310, in various examples, the analyte sensor 360 and wearable automatic drug delivery device 310 may be incorporated into the same unit. That is, in various examples, the sensor 360 may be a part of the wearable automatic drug delivery device 310 and contained within the same housing of the wearable automatic drug delivery device 310 (e.g., the sensor 360 or, only the sensing/measuring device 366 and memory storing related programming code may be positioned within or integrated into, or into one or more components, such as the memory 350 of, the wearable automatic drug delivery device 310). In such an example configuration, the controller 344 may be able to implement the process examples of FIGS. 1A-2 alone without any external inputs from the management device 328, the cloud-based services 311, the optional smart accessory device 316, or the like.

The communication link 376 that couples the cloud-based services 311 to the respective devices 310, 360, 328 or 316 of system 312 may be a cellular link, a Wi-Fi link, a Bluetooth link, or a combination thereof. Services provided by cloud-based services 311 may include data storage that stores anonymized data, such as blood glucose measurement values, drug delivery history, bolus delivery history, time data, —and other forms of data. In addition, the cloud-based services 311 may process the anonymized data from multiple users to provide generalized information related to clinical diabetes-related data and the like.

The wireless communication links, 302, 304, 306, 370, 372, and 374 may be any type of wireless link operating using known wireless communication standards or proprietary standards. As an example, the wireless communication links 302, 304, 306, 370, 372, and 374 may provide communication links based on Bluetooth®, Zigbee®, Wi-Fi, a near-field communication standard, a cellular standard, or any other wireless protocol via the respective communication devices 318, 354 and 364 and communication interface 380.

Software related implementations of the techniques described herein, such as the processes examples described with reference to FIGS. 1A-2 may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. Blood glucose measurements may be provided for closed-loop input from a blood glucose monitor, a continuous glucose monitor, or the like. A management device may maintain the data history and adjust or recommend system settings. For example, the disclosed MDA application and algorithms may be operable to perform various functions related to open loop operations, such as the generation of prompts requesting the input of information such as weight or age. Similarly, a dosage amount of insulin may be received by the MDA application or algorithm from a user via a user interface. Other open-loop actions may also be implemented by adjusting user settings or the like in an MDA application or algorithm.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A method, comprising:

accessing, by a controller of a drug delivery device, a drug delivery history, a bolus drug history, a blood glucose measurement history, and a meal announcement history for a period of time from a memory coupled to the controller;

calculating a daily basal profile using respective data from each of the drug delivery history, the bolus drug history, the blood glucose measurement history, and the meal announcement history, wherein the daily basal profile is a time schedule for delivering respective basal delivery dosages;

generating, by the controller, a control signal for delivery of a basal dosage at a scheduled time from the daily basal profile; and causing delivery of the basal dosage in the daily basal profile by outputting the control signal to a pump mechanism of the drug delivery device communicatively coupled to the controller.

2. The method of claim 1, further comprising:

determining an adjusted basal need for each of a plurality of preselected times, wherein the adjusted basal need is an individual entry in the daily basal profile and the basal dosage is determined according to the adjusted basal need.

3. The method of claim 2, wherein the bolus drug history further includes an indication of which bolus dosages in the bolus drug history were delivered manually; and the method further comprising:

determining the adjusted basal need for each respective time of the plurality of preselected times, using an aggregate factor; and outputting the adjusted basal need for a respective time of the plurality of preselected times.

4. The method of claim 2, wherein determining the adjusted basal need for each of the plurality of preselected times, comprises:

for each respective time of the plurality of preselected times, summing an obtained amount of the drug, a respective blood glucose measurement factor, and an obtained respective amount of the drug delivered in the bolus dose to provide an aggregate factor, determining a proportion of an amount of drug provided via bolus dosages to an amount provided via the aggregate factor, modifying the proportion based on a contribution factor, determining a resultant by multiplying the aggregate factor by the modified proportion; and outputting the resultant of the multiplying as the adjusted basal need for a respective time of the plurality of preselected times.

5. The method of claim 4, wherein the contribution factor is a bias weighting that reduces a value of an estimated correction factor to less than 1.0.

6. The method of claim 2, wherein determining the adjusted basal need further comprises:

summing an obtained amount of the drug, and an obtained respective amount of the drug delivered in the bolus dose to provide an aggregate factor;

subtracting from the aggregate factor a respective blood glucose measurement factor; and outputting a result of the summing and subtracting as the adjusted basal need for a respective time of the plurality of preselected times.

7. The method of claim 2, wherein the daily basal profile includes times at which a basal delivery dosage of the respective basal delivery dosages is to be delivered.

8. The method of claim 1, further comprising: determining a meal announcement factor by:

retrieving a meal announcement value corresponding to a respective time in a series of time settings, wherein the meal announcement value is an estimate of a number of carbohydrates in a meal that triggered the meal announcement notification;

determining an insulin-to-carbohydrate ratio; and dividing the meal announcement value by the insulin to carbohydrate ratio, wherein the quotient is the meal announcement factor.

9. The method of claim 1, wherein calculating the daily basal profile, further comprises:

determining a series of time settings in the time schedule;

calculating a blood glucose measurement factor that corresponds to each time in the series of time settings using a blood glucose measurement value, a fasting blood glucose target setting, a duration of insulin action value, and a correction factor;

calculating a drug delivery history factor of calculated basal delivery dosages that corresponds to each time in the series of time settings using bolus dosages from the bolus drug history; and setting the daily basal profile based on the adjusted basal need determined for each of a plurality of preselected times.

10. The method of claim 2, wherein calculating the blood glucose measurement factor, further comprises:

for each respective time of the plurality of preselected times:

outputting a blood glucose measurement factor that is determined based on a blood glucose measurement value obtained from the blood glucose measurement history, a fasting blood glucose target setting, a duration of insulin action value multiplied by an estimated correction factor.

11. The method of claim 1, further comprising:

filtering, by the controller, respective data in each of the drug delivery history, the bolus drug history, the blood glucose measurement history, and the meal announcement history, according to predetermined filter settings related to a time interval of the period of time.

12. A drug delivery device comprising:

a controller; and a memory storing instructions that, when executed by the controller, configure the drug delivery device to:

access a drug delivery history, a bolus drug history, a blood glucose measurement history, and a meal announcement history for a period of time from a memory coupled to the controller;

calculate a daily basal profile using respective data from each of the drug delivery history, the bolus drug history, the blood glucose measurement history, and the meal announcement history;

generate, by the controller, a control signal for delivery of a basal dosage of a calculated basal delivery dosages at a scheduled time from the daily basal profile; and apply the control signal to a pump mechanism of the drug delivery device communicatively coupled to the controller.

13. The drug delivery device of claim 12, wherein the drug delivery device, when calculating the daily basal profile, is further configured to:

determine a series of time settings in the daily basal profile;

calculate a blood glucose measurement factor that corresponds to each time in the series of time settings using a blood glucose measurement value, a fasting blood glucose target setting, a duration of insulin action value, and a correction factor;

calculate a drug delivery history factor of the calculated basal delivery dosages that corresponds to each time in the series of time settings using bolus dosages from the bolus drug history;

determine a meal announcement factor that corresponds to each time in the series of time settings based on the meal announcement history and a drug ratio related to meal content; and determine an adjusted basal need for each of a plurality of preselected times in the series of time settings.

14. The drug delivery device of claim 13, wherein the drug delivery device, when determining the adjusted basal need for each of the plurality of preselected times, is further configured to:

for each respective time of the plurality of preselected times:

sum an obtained amount of the drug, an obtained respective amount of the drug delivered in the bolus dose, and a respective blood glucose measurement factor to provide an aggregate factor;

subtract from the aggregate factor the meal announcement factor; and output a result of the summing and subtracting as the adjusted basal need for a respective time of the plurality of preselected times.

15. The drug delivery device of claim 13, wherein the drug delivery device, when determining the adjusted basal need for each of the plurality of preselected times, is further configured to:

for each respective time of the plurality of preselected times:

sum an obtained amount of the drug from the drug amount data in the drug delivery history, an obtained respective amount of the drug delivered in the bolus dose, and a respective blood glucose measurement factor to provide an aggregate factor;

subtract from the aggregate factor the meal announcement factor and a proportion of an amount of the drug in the bolus dosage delivered manually from the bolus drug history; and output the result of the summing and subtracting as the adjusted basal need for a respective time of the plurality of preselected times.

16. The drug delivery device of claim 13, wherein the drug delivery device, when determining a plurality of blood glucose measurement factors from the blood glucose measurement history, is further configured to:

for each respective time of the plurality of preselected times:

output a blood glucose measurement factor that is determined based on a blood glucose measurement value obtained from the blood glucose measurement history, the fasting blood glucose target setting, and a duration of insulin action value multiplied by an estimated correction factor.

17. The drug delivery device of claim 13, wherein the drug delivery device, when determining the adjusted basal need for each of the plurality of preselected times, is further configured to:

for each respective time of each of the plurality of preselected times:

output the adjusted basal need for the respective time of the plurality of preselected times, wherein the adjusted basal need is determined based on an aggregate factor, and a contribution factor.

18. The drug delivery device of claim 12, wherein:

the drug delivery history is a data structure containing drug amount data related to background doses of a drug delivered at respective times over a course of the drug delivery history based on an algorithm executed by the controller, the bolus drug history is a data structure containing bolus delivery time data related to delivery of bolus doses of the drug and an amount of the drug delivered in each bolus dose of the bolus doses, the blood glucose measurement history is a data structure of blood glucose measurement values in which each blood glucose measurement value has a corresponding time when the blood glucose measurement value was obtained, and the meal announcement history is a data structure of times when a meal announcement notification was received by the controller.

19. The drug delivery device of claim 12, wherein the daily basal profile includes a time schedule for delivering respective basal delivery dosages.

20. A drug delivery device comprising:

a controller; and a memory storing instructions that, when executed by the controller, configure the drug delivery device to:

access a drug delivery history, a bolus drug history, a blood glucose measurement history, and a meal announcement history for a period of time from a memory coupled to the controller;

filter, by the controller, respective data in each of the drug delivery history, the bolus drug history, the blood glucose measurement history, and the meal announcement history, according to predetermined filter settings related to a time interval of the period of time;

calculate a daily basal profile using the filtered, respective data from each of the drug delivery history, the bolus drug history, the blood glucose measurement history, and the meal announcement history;

generate, by the controller, a control signal for delivery of a basal dosage of the calculated basal delivery dosages at a scheduled time from the daily basal profile; and cause delivery of the calculated basal delivery dosages at the scheduled time by applying the control signal to a pump mechanism of the drug delivery device communicatively coupled to the controller.

* * * * *